(12) United States Patent
Reinhardt et al.

(10) Patent No.: US 11,375,896 B2
(45) Date of Patent: Jul. 5, 2022

(54) EDGE-INTELLIGENT IOT-BASED WEARABLE DEVICE FOR DETECTION OF CRAVINGS IN INDIVIDUALS

(71) Applicants: Megan Reinhardt, Bristol, MA (US); Nicole Gilbertson, Huntington Beach, CA (US); Premananda Indic, Whitehouse, TX (US); Prabha Sundaravadivel, Murphy, TX (US)

(72) Inventors: Megan Reinhardt, Bristol, MA (US); Nicole Gilbertson, Huntington Beach, CA (US); Premananda Indic, Whitehouse, TX (US); Prabha Sundaravadivel, Murphy, TX (US)

(*) Notice: Subject to any disclaimer, the term of this patent is extended or adjusted under 35 U.S.C. 154(b) by 360 days.

(21) Appl. No.: 16/688,861

(22) Filed: Nov. 19, 2019

(65) Prior Publication Data

US 2020/0085301 A1 Mar. 19, 2020

Related U.S. Application Data

(63) Continuation-in-part of application No. 15/681,111, filed on Aug. 18, 2017, now Pat. No. 10,478,066.

(51) Int. Cl.
| | |
|---|---|
| *A61B 5/00* | (2006.01) |
| *G16H 40/63* | (2018.01) |
| *A61B 5/0205* | (2006.01) |
| *G06K 19/077* | (2006.01) |
| *G06F 1/16* | (2006.01) |

(52) U.S. Cl.
CPC .......... *A61B 5/0022* (2013.01); *A61B 5/0205* (2013.01); *G06F 1/163* (2013.01); *G06K 19/07762* (2013.01); *G16H 40/63* (2018.01)

(58) Field of Classification Search
CPC .... A61B 5/0022; A61B 5/0205; G16H 40/63; G06F 1/163
See application file for complete search history.

(56) References Cited

U.S. PATENT DOCUMENTS

| | | |
|---|---|---|
| 9,782,122 B1 | 10/2017 | Pulliam |
| 2005/0039742 A1 | 2/2005 | Hickle |
| 2008/0208016 A1 | 8/2008 | Hughs |

(Continued)

*Primary Examiner* — Christopher A Flory
(74) *Attorney, Agent, or Firm* — Averill & Green; Kenneth L. Green (57) ABSTRACT

A wearable physiological monitoring system comprises commercially available off-the shelf components. With the growth of interrelated systems of computing devices, mechanical and digital machines, objects, animals or people connected by the Internet, there is a significant interest in the use of wearable sensors such as cell watches, and cell phones. These wearable sensors may be used to monitor physiological signals and provide health information. An edge-intelligent Internet based wearable assists in substance-abuse detection by monitoring and interpreting an individual's physiological signals on continuous basis. The wearable device helps in monitoring cravings and substance abuse of the individual and help the healthcare provider to start an early intervention as required. The proposed system is developed as a dedicated substance abuse wearable system. An example of a wearable device is a medical quality wearable which yielded a correlation of 0.89 for accelerometer measurements and 0.92 for average heart rate measurements in tests.

14 Claims, 5 Drawing Sheets

(56) References Cited

U.S. PATENT DOCUMENTS

| | | |
|---|---|---|
| 2010/0268056 A1 | 10/2010 | Picard |
| 2011/0004072 A1 | 1/2011 | Fletcher |
| 2012/0296175 A1 | 11/2012 | Poh |
| 2013/0079602 A1 | 3/2013 | Picard |
| 2013/0080185 A1 | 3/2013 | Picard |
| 2013/0294005 A1* | 11/2013 | Garaycochea ...... F41H 13/0018 |
| | | 361/232 |
| 2014/0316229 A1 | 10/2014 | Tognetti et al. |
| 2015/0148621 A1 | 5/2015 | Sier |
| 2015/0342511 A1 | 12/2015 | Goldberg |
| 2017/0112407 A1 | 4/2017 | Wu |
| 2017/0347906 A1 | 12/2017 | Intrator |
| 2017/0372592 A1* | 12/2017 | Neravati ............ G08B 21/0446 |
| 2018/0001184 A1 | 1/2018 | Tran |
| 2018/0068080 A1 | 3/2018 | Parate |
| 2018/0228695 A1 | 8/2018 | Valentine |
| 2018/0308569 A1 | 10/2018 | Luellen |
| 2019/0037919 A1* | 2/2019 | Doan ...................... G09B 5/02 |

\* cited by examiner

EDGE-INTELLIGENT IOT-BASED WEARABLE DEVICE FOR DETECTION OF CRAVINGS IN INDIVIDUALS

CROSS-REFERENCE TO RELATED APPLICATIONS

The present application is a Continuation In Part of U.S. patent application Ser. No. 15/681,111 filed Aug. 18, 2017, which application is incorporated in its entirety herein by reference.

BACKGROUND OF THE INVENTION

The present invention relates to addressing destructive cravings and in particular to a wearable device for monitoring a level of cravings experienced by a subject.

Drug addiction is an increasingly serious individual and societal issue. The rate of drug addiction in the United States has reached levels where this addiction affects not only the addict, but society as a whole. Many addicts recognize their personal damage due to the use of drugs and desire to overcome their addiction through various programs. The individuals often successfully complete a program, but are not able to remain drug free after re-entering society, especially when they are subject to the stress that both existed in the past, and stress produced by social issues they encounter when they attempt to rejoin society. Such stress often results in cravings to resume drug use. Other similar conditions include eating disorders/food addiction, co-occurring disorders with addiction, and Post-Traumatic Stress Disorder (PTSD). A need exists for identifying the presence of stress and the resulting cravings to allow intervention before a return to drug use.

Further, known commercially available wearable sensors only monitor an individual's heart rate and activity and may not provide sufficient measurements to support detection of stress likely to cause cravings.

BRIEF SUMMARY OF THE INVENTION

The present invention addresses the above and other needs by providing a wearable craving and drug use sensor suit. With the growth of interrelated systems of computing devices, mechanical and digital machines, objects, animals or people connected by the Internet, there is a significant interest in the use of wearable sensors such as smart watches and cell phones. These wearable sensors may be used to monitor physiological signals and provide health information. An edge-intelligent Internet based wearable assists in substance-abuse detection by monitoring an individual's physiological signals on a daily basis. The edge intelligent approach enables us to do all the processing of signals as well as assessment of the underlying condition in the device itself. The wearable device helps in monitoring cravings and substance abuse of the individual and help the healthcare provider to start an early intervention as required. The proposed system is developed as a dedicated substance abuse wearable system with commercially available off-the shelf components. An example of a wearable device is a medical quality wearable which yielded a correlation of 0.89 for accelerometer measurements and 0.92 for average heart rate values in tests.

In accordance with another aspect of the invention, there is provided a system to detect an individual subject's stress, cravings, and use of drugs, based on physiological sensors, advanced signal processing and a machine learning framework. A wearable sensor suit is worn by a subject recovering from drug use. The sensor suit produces signals by measuring physiological parameters such as one, two, or three dimensions of body movement (locomotor activity), Electro Dermal Response (EDR), heart rate, skin temperature, a galvanic skin response. Statistical data (e.g., the mean and variance) of the measurements are computed. The statistical features may be used to assess cravings and/or stress in the individual subject. Data has shown that accelerometer measurements in each dimension are significantly but not perfectly (less than 100%) correlated with other dimensions, and hence the detection of stress and cravings can be achieved with one dimension data with reasonable accuracy without EDR or temperature data. The physiological data is processed in windows having a length L, for example, a five minute window.

In accordance with still another aspect of the invention, there is provided a system to determine shape and scale parameters of a distribution of amplitudes of the three dimensional movement data are computed. Amplitudes, frequencies, and phases of the three dimensions of motion signals may be obtained using an appropriate transform. The distribution of amplitudes provides a sensitive measure capable of detecting the frequency of use of drugs (heavy use vs. moderate use). Dynamic features such as instantaneous fluctuations of amplitudes, frequencies, and phases at multiple time scales may be obtained by the time-frequency decomposition of these signals using an appropriate transform, for example the Hilbert or a wavelet transform approach In accordance with yet another aspect of the invention, there is provided a method for adapting a drug use risk detection method to an individual subject prior to release from a treatment facility. A training data set comprising statistical and dynamic features is collected and incorporated in a machine learning framework. The data is collected over a one to two day period where the individual is monitored to ensure that there is no drug use. The processed three dimensional motion signals, the EDR, and temperature signals, are processed by machine learning algorithms to establish boundaries for non-drug use. The machine learning framework is tailored specifically to individual subjects to assess pathological fluctuations in the physiological signals that can be used later assess the risk or return to drug use.

In accordance with another aspect of the invention, there is provided a method for detection of cravings. Following release of the individual subject from a treatment facility, the individual subject is provided with a wearable device measuring physiological data. The wearable device continuously measures physiological signals, and the signals are processed for relevant features related to cravings. An alert is provided to the individual subject and/or a provider through of any imminent risk of using illicit drugs or cravings. By accurately tracking the statistical and dynamic fluctuations in these physiological signals in real time, the method can provide accurate detection of cravings.

In accordance with yet another aspect of the invention, there is provided a method for providing alerts to a care giver. The present system includes non-invasive wearable biosensors that stream data continuously in real time to a processor which processes the physiological signals and executes a craving or risk detection software. Once a specific threshold of risk has reached, the algorithm can trigger an alert through a cell phone to a user or a care giver or a provider.

In accordance with still another aspect of the invention, there is provided a method for providing alerts based on a 16 dimension vector space of ten physiological signals comprising mean and variance of three dimensional motion, EDR, and temperature, and six spatial features comprising shape and scale of histogram data.

In accordance with another aspect of the invention, there is provided a wearable sensor monitoring three dimensional data at a 32 samples per second, EDR data at four samples per second, and temperature data at one sample per second. The data is provided in windows of about 5 minute length.

In accordance with still another aspect of the invention, there is provided a monitoring system including a wearable sensor, a cell phone type device, and a monitoring facility. Data collected by the wearable sensor may be processed in the wearable sensor, in the cell phone type device, or at the monitoring facility. In some embodiments, the wearable sensor and cell phone type device may be a single device.

In accordance with another aspect of the invention, there is provided a wearable sensor. The wearable sensor includes physiological sensors and is an edge-intelligent device processing sensor measurements and sending assessments of cravings to a remote sever accessed by clinicians.

In accordance with yet another aspect of the invention, there is provided a method for a wearable sensor sensing and processing subject data during supervision. The method includes collecting training data, processing the training data, applying machine learning to the training data and subject inputs to determine classification rules, and transmitting the training rules to a cloud/clinicians.

In accordance with still another aspect of the invention, there is provided a method for a wearable sensor sensing and processing subject data after release from supervision. The method includes repeating the method used during supervision, but also building a deep neural network in the cloud or at clinician facilities, and providing alters to the subjects cell phone.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the terms "about" or "generally" are associated with an element of the invention, it is intended to describe a feature's appearance to the human eye or human perception, and not a precise measurement.

Figure 1:
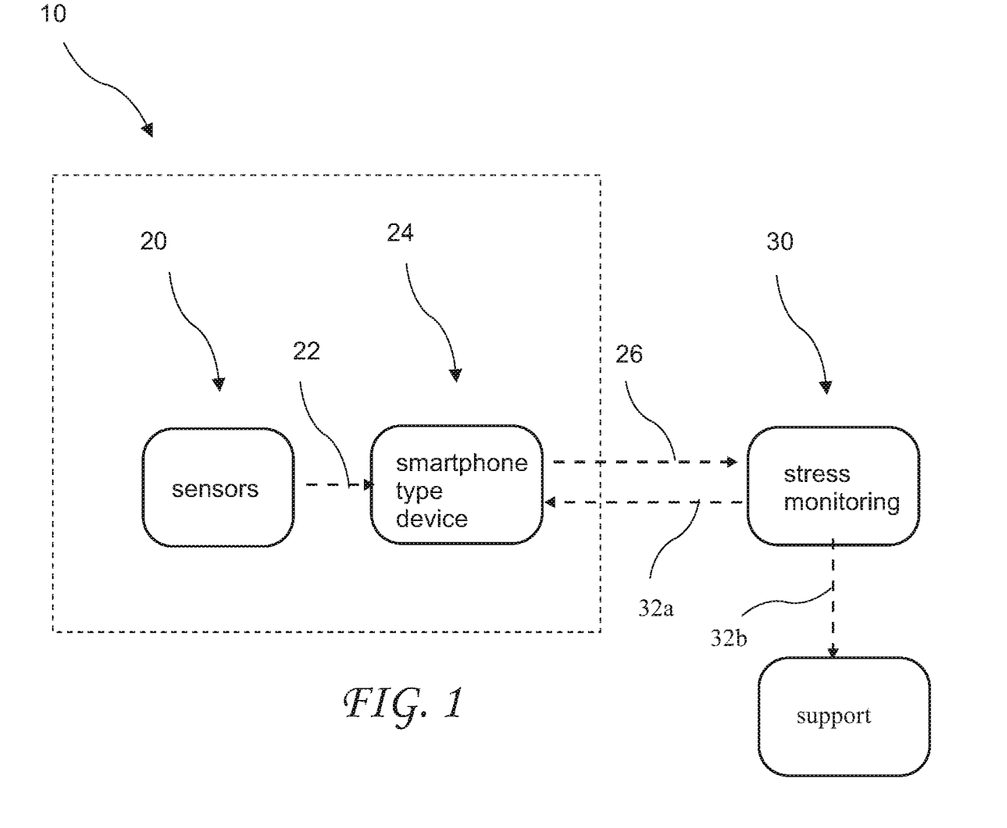
FIG. 1 shows components of a system for sensing physiological parameters and detecting cravings based on the physiological parameters in individuals with addiction according to the present invention.

Components of a system for detection of cravings in individuals with addiction according to the present invention are shown in FIG. 1. The system includes wearable devices 10 comprising sensor suit 20 and a cell phone type device 24 carried by the individual. The sensor suit 20 measures physiological parameters including three dimensional body movement, Electro Dermal Response (EDR), and temperature. A suitable sensor suit is described in US Patent Application Publication No. 2014/0316229 for "Apparatus for Electrodermal Activity Measurement with Current Compensation" filed 17 Mar. 2014. The sensor suit 20 includes at least one accelerometer, a temperature sensor, and EDR sensor. The '229 publication is incorporated by reference in its entirety into the present specification.

The sensor suit 20 preferably wirelessly communicates with a cell phone type device 24 to provide data 22 to the cell phone type device 24. The wireless communication may be, for example, Bluetooth communication. While Bluetooth is a preferred wireless interface, those skilled in the art will recognize other types of communication, including wired, and a system according to the present including any form of communication between the sensors and the cell phone type device, and the sensor suit 20 and cell phone type device 24 may be a single device.

The cell phone type device 24 receives the three dimensional movement, the EDR, and temperature signals 22 from the sensor suit 20 and transits the data 26 to a stress monitoring center 30. If the cravings exceed a threshold, or advanced processing indicates a craving, the stress monitoring center 30 may provide alerts 32*a* back to the subject and alerts 32*b* to support personnel. The data may be processed in the sensor suit 20, the cell phone type device 24, or at the stress monitoring center 30, and the processing may be distributed over the sensor suit 20, the cell phone type device 24, and the stress monitoring center 30. Those skilled in the art will recognize that any distribution of the method between devices is intended to come within the scope of the present invention.

Figure 2:
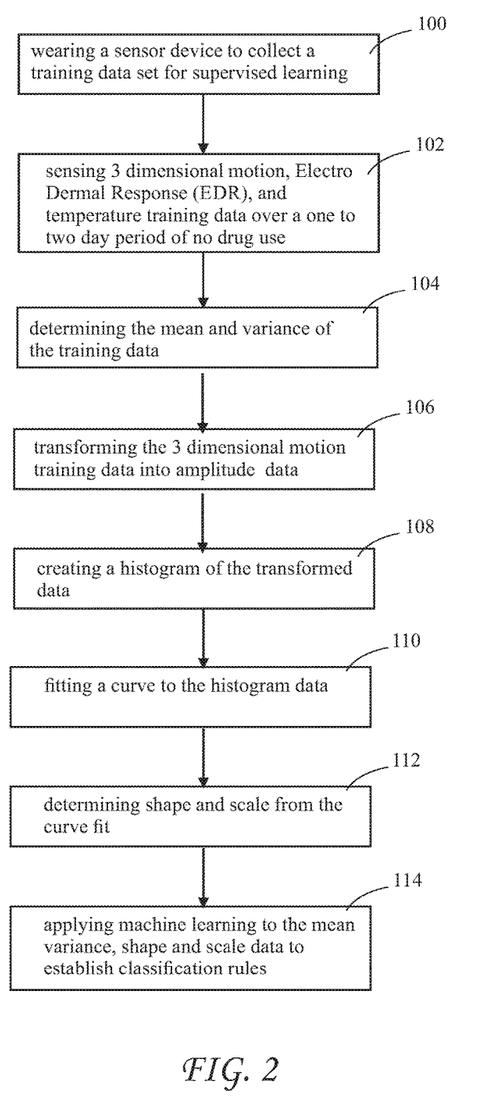
FIG. 2 shows a method for processing the individual physiological parameters to detected cravings according to the present invention.

A method for processing the individual physiological parameters measured during a period of supervised no drug use to establish classification rules is shown in FIG. 2. The method includes wearing a sensor device to collect a training data set for supervised learning at step 100, sensing 3 dimensional motion, Electro Dermal Response (EDR), and temperature training data over a one to two day period of supervised no drug use by the subject at step 102, determining the mean and variance of the training data at step 104, transforming the 3 dimensional motion training data into amplitude data at step 106, creating a histogram of the transformed data at step 108, fitting a curve to the histogram data at step 110, determining shape and scale from the curve fit at step 112, applying machine learning to the mean variance, shape and scale data to establish classification rules at step 114. Examples of transforms used in steps 106 and 206 are a Hilbert transform or a wavelet transform. Examples of curves applied to the curve fit of steps 110 and 210 are fitting a gamma function to the amplitude data.

Figure 3:
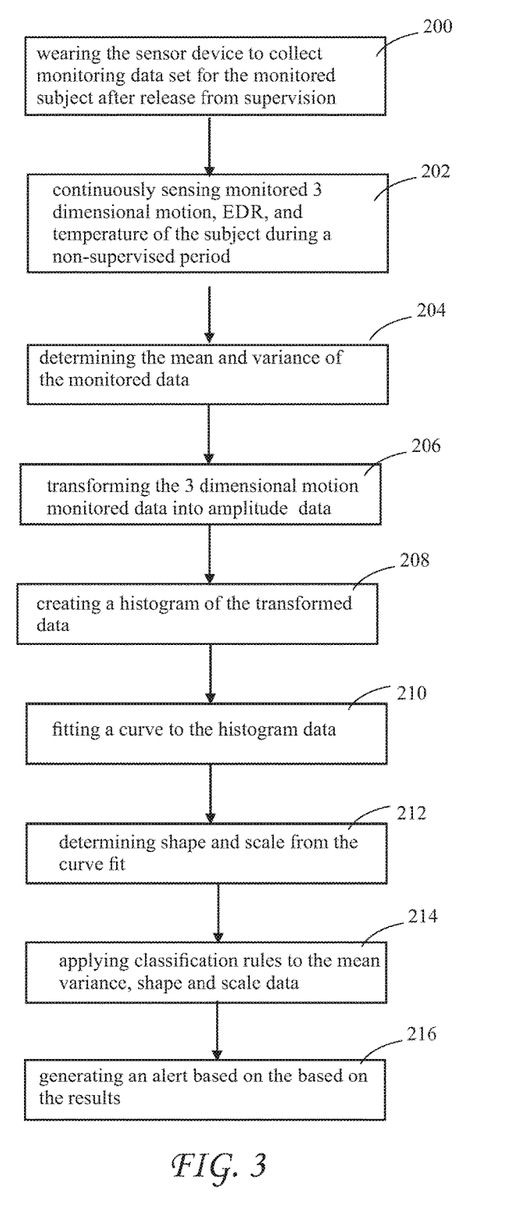
FIG. 3 shows a method for processing the individual physiological parameters measured during an unsupervised period to detect stress, cravings, and drug use.

A method for processing the individual physiological parameters measured during an unsupervised period to detect stress, cravings, and drug use, is shown in FIG. 3. The method includes wearing the sensor device to collect monitoring data set for the monitored subject after release from supervision at step 200, continuously sensing monitored three dimensional motion, EDR, and temperature of the subject during a non-supervised period is shown in step 202, determining the mean and variance of the monitored data is shown in step 204, transforming the three dimensional motion monitored data into amplitude data is shown in step 206, creating a histogram of the transformed data is shown in step 208, fitting a curve to the histogram data is shown in step 210, determining shape and scale from the curve fit is shown in step 212, applying classification rules to the mean variance, shape and scale data is shown in step 214, and generating an alert based on the results is shown in step 216. The alerts may be provided to the subject and/or to a monitor and may be an alert for stress, for cravings, or of drug use.

Figure 4:
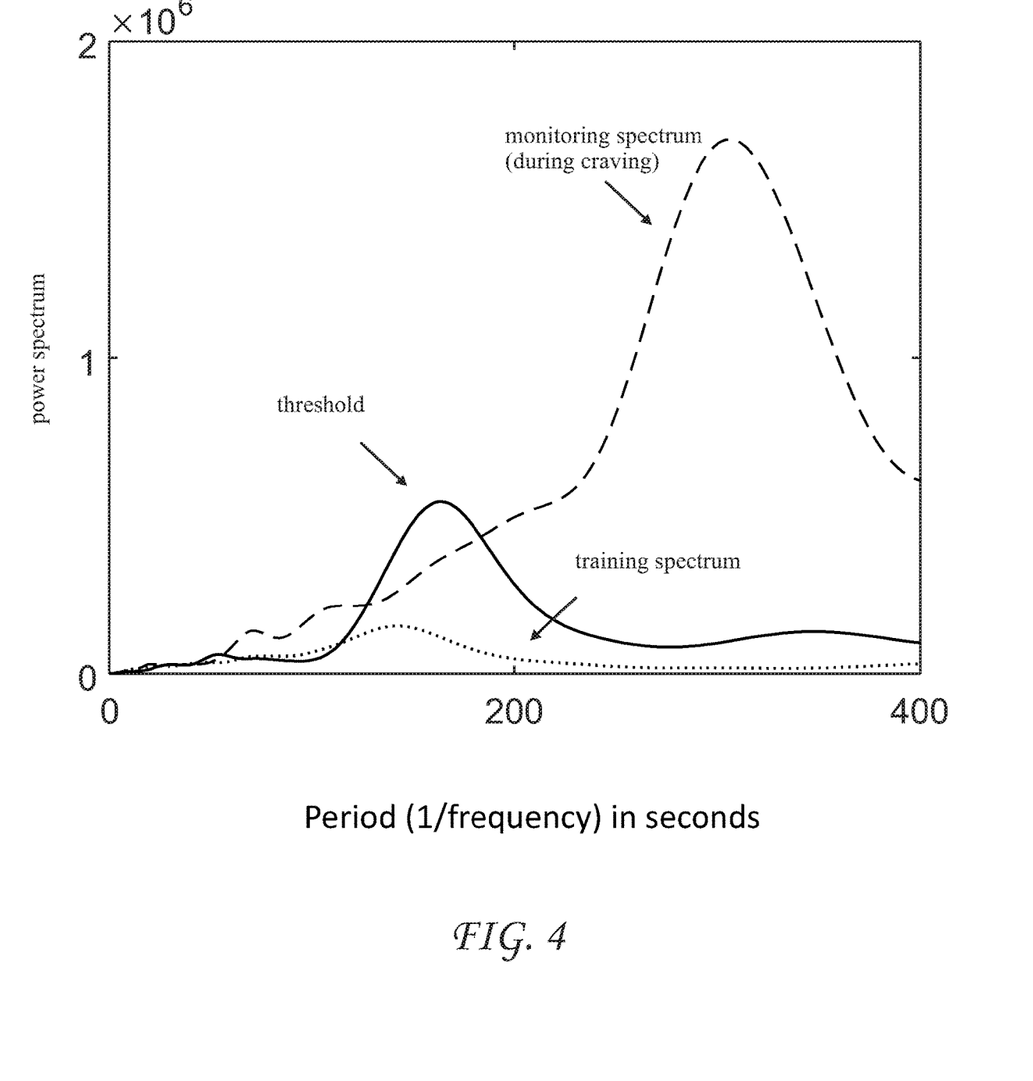
FIG. 4 shows a plot of a training spectrum, a monitoring spectrum, and a threshold.

A plot of a training spectrum, a monitoring spectrum, and a threshold are shown in FIG. 4.

Figure 5:
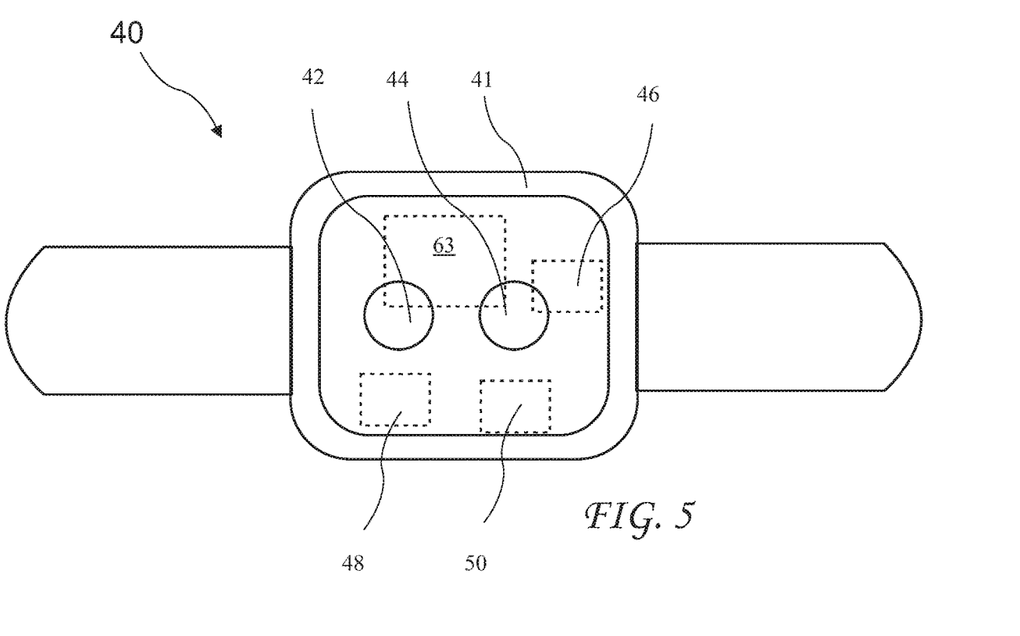
FIG. 5 is a wearable sensor according to the present invention.
Figure 6:
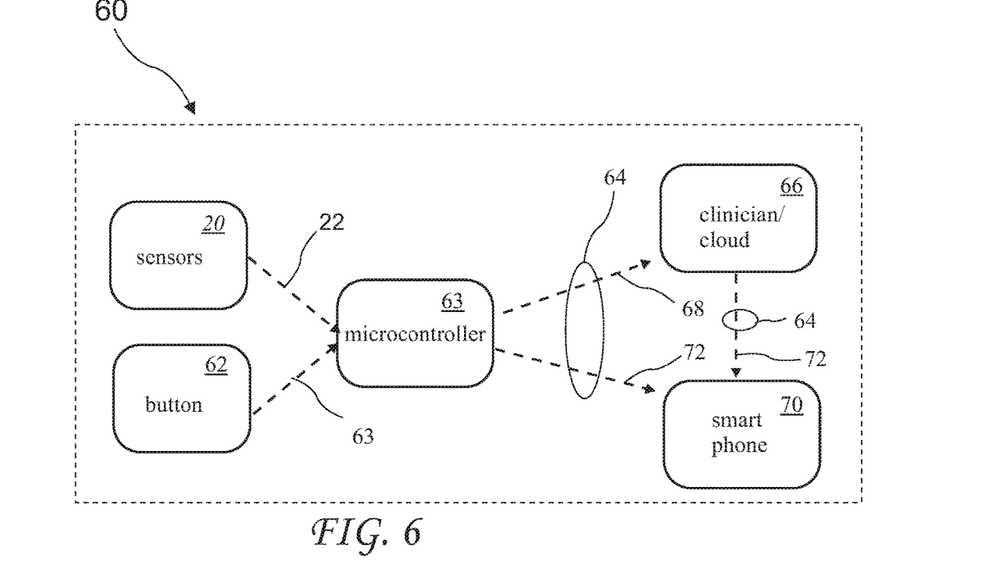
FIG. 6 shows components of a wearable system for sensing physiological parameters and detecting cravings based on the physiological parameters in individuals with addiction according to the present invention.

A wearable device 40 is shown in FIG. 5 and elements of a cravings/stress monitoring system 60 are shown in FIG. 6. The wearable device 40 includes housing 41 including a 3-axis accelerometer sensor 48, a thermopile sensor 50, a pulse oximeter sensor 46, a subject stress input (e.g., subject button) 42, a subject craving input (e.g. subject button) 44, and a microcontroller (e.g., microprocessor) 63. The wearable device 40 collects and processes physiological parameters and subject inputs to anticipate substance abuse by monitoring for the physiological parameters associated with stress leading to craving and detects substance abuse by monitoring for physiological parameters associated with substance abuse. The system 60 includes the wearable device 40 coupled to a clinician and/or cloud 66 and the subject's cell phone 70 over the Internet 64. The wearable device 40 and/or the clinician and/or cloud 66 sends alerts 72 to the subject though the internet 64 to the cell phone 68 to alert the subject to the onset of physiological conditions which may lead to harmful behavior, and the wearable device 40 sends messages 68 to the clinician/cloud 66 indicating a pattern of substance abuse and craving in the subject and for learning.

The thermopile sensor 50 detects temperature variability of the individual in given period of time. As a result, the temperature values are scheduled in such a way that the current temperature value is being compared with the previous acquired value constantly to check for the rate of change and corresponding variability. The 3-axis accelerometer sensor 48 monitors motion of the subject on daily basis. This motion may show that the subject has reported stress and craving in spite of maintaining an active lifestyle. The pulse oximeter sensor 46 is a medical grade sensor which measures the heart rate of the subject on daily basis. The subject stress and craving input 42 and 44 values indicate that the subject experience stress or cravings at an point of time. The subject inputs are recorded along with the timestamp at which the subject hits the inputs 42 or 44.

Examples of features for detecting the cravings and substance abuse are gross body movement measured by the 3-axis accelerometer sensor 48, temperature variability measured by the thermopile sensor 50, and heart rate measured by the pulse oximeter sensor 46. The subject may also input stress and craving which may be correlated with the sensor measurements to monitor substance abuse of the subject. For example, if the subject records stress or craving, the corresponding sensor measurements are labeled as "substance event", otherwise measurements are labeled as "normal event". If a similar set of sensor measurements are detected, but there is no subject input at a particular time instance, then they are marked for "vulnerable event". The clinician periodically reviews this set of sensor measurements to detect a pattern of substance abuse and craving in the subject. While a preferred sensor suit is shown in FIG. 5, data collection has shown that cravings and drug use may be identified with as few as one of the sensors, and a system with at least one of the sensors in FIG. 5 is intended to come within the scope of the present invention.

An example of the purpose of obtaining the subject inputs at a given time instance is to mark the number of times the subject is stressed which might lead to substance craving. Hence the following subject input protocol is maintained to effectively derive at the proposed hypotheses based on subject input values: a simple questionnaire to mark the stress and anxiety levels of the subject before using the wearable is recorded; a preliminary assessment on the substance abuse of the subject before using the wearable is recorded; the subject is informed of their accountability in pressing the input buttons whenever they feel stressed or possess substance craving at any time of the day; and the subject is informed of subject rewards such as points that are given to the subject every time a pattern of healthy active lifestyle is detected, including regular exercise or providing reliable subject inputs on stress and cravings.

Figures 7, 8:
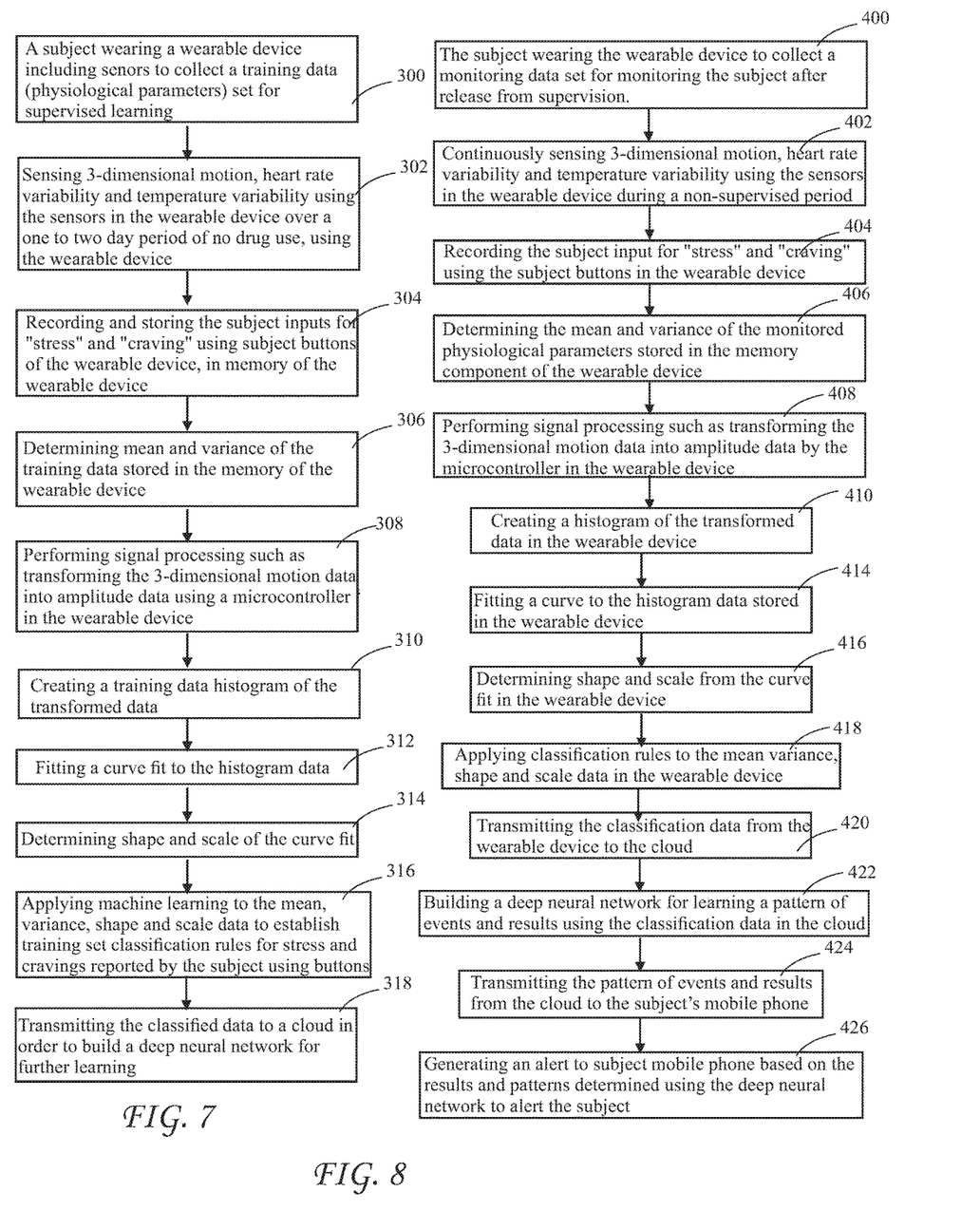
FIG. 7 shows a method for collecting and processing a subject's physiological parameters during supervision.
FIG. 8 shows a method for collecting and processing a subject's physiological parameters after supervision and providing alerts.

A method for collecting and processing a subject's physiological parameters during supervision is shown in FIG. 7. The method includes: a subject wearing a wearable device including sensors to collect a training data (physiological parameters) set for supervised learning at step 300, sensing 3-dimensional motion, heart rate variability and temperature variability using the sensors in the wearable device over a one to two day period of no drug use, using the wearable device at step 302, recording and storing the subject inputs for "stress" and "craving" using subject buttons of the wearable device, in memory of the wearable device at step 304, determining mean and variance of the training data stored in the memory of the wearable device at step 306, performing signal processing such as transforming the 3-dimensional motion data into amplitude data using a microcontroller in the wearable device at step 308, creating a training data histogram of the transformed data at step 310, fitting a curve fit to the histogram data at step 312, determining shape and scale of the curve fit at step 314, applying machine learning to the mean, variance, shape and scale data to establish training set classification rules for stress and cravings reported by the subject using buttons at step 316, and transmitting the classified data to a cloud in order to build a deep neural network for further learning at step 318.

A method for collecting and processing a subject's physiological parameters after supervision and providing alerts, is shown in FIG. 8. The method includes: the subject wearing the wearable device to collect a monitoring data set for monitoring the subject after release from supervision at step 400, continuously sensing 3-dimensional motion, heart rate variability and temperature variability using the sensors in the wearable device during a non-supervised period at step 402, recording the subject input for "stress" and "craving"

using the subject buttons in the wearable device at step 404, determining the mean and variance of the monitored physiological parameters stored in the memory component of the wearable device at step 406, performing signal processing such as transforming the 3-dimensional motion data into amplitude data by the microcontroller in the wearable device at step 408, creating a histogram of the transformed data in the wearable device at step 410, fitting a curve to the histogram data stored in the wearable device at step 414, determining shape and scale from the curve fit in the wearable device at step 416, applying classification rules to the mean variance, shape and scale data in the wearable device at step 418, transmitting the classification data from the wearable device to the cloud at step 420, building a deep neural network for further learning using the classification data in the cloud at step 422, transmitting a pattern of events and results from the cloud to the subject's mobile phone at step 424, and generating an alert to a subject mobile phone based on the results and patterns determined using the deep neural network to alert the subject at step 426.

The deep neural network processing in step 422 may alternatively be performed in the wearable device using an edge intelligent approach. In instances where insufficient data is available for the deep neural network processing, the cell phone alerts may be solely based on comparing non-supervised measurements to the classification rules.

While the methods of the present invention specifically target cravings for drugs, similar methods may be developed an applied to other disorders, for example, eating disorders/food addiction, co-occurring disorders with addiction, and Post-Traumatic Stress Disorder (PTSD). Those skill in the art will recognize that the methods of the present invention directed to these other disorders come within the scope of the present invention.

While the invention herein disclosed has been described by means of specific embodiments and applications thereof, numerous modifications and variations could be made thereto by those skilled in the art without departing from the scope of the invention set forth in the claims.

We claim:

1. A wearable device for detecting craving of a subject, comprising:
    a housing including:
        at least one sensor selected from the group consisting of an accelerometer, a thermopile sensor, and a pulse oximeter sensor
        at least one subject button selected from the group consisting of a subject stress input button and a subject craving input button; and
        a microprocessor electrically connected to the at least one sensor and the at least one subject button;
    wireless communications between the microprocessor and at least one of a subject cell phone, a clinician, and a cloud,
    wherein:
        during a supervised period, the patient presses the input button while experiencing stress or cravings, and the microprocessor processes signals from the at least one sensor while the input button is pressed to determine training set classification rules; and
        during an unsupervised period:
            the microprocessor processes signals from the at least one sensor to determine characteristics of the unsupervised sensor data; and
            the microprocessor compares the characteristics of the unsupervised sensor data to the training set classification rules; and
        at least one element selected from the group consisting of the microprocessor, the clinician, and the cloud, provides alerts to the subject cell phone based on the comparison,
    and wherein:
    processing the signals from the at least one sensor and the at least one input buttons to determine training set classification rules during the supervised period comprises:
        producing training motion data in at least one dimension by sensing the training motion of the subject during a period of no drug use;
        generating training statistics of the training motion data during the period of no drug use; and
        determining classification rules for the training statistics during the period of no drug use; and
    processing signals from the at least one sensor to determine characteristics of the unsupervised sensor data comprises producing monitoring motion data in the at least one dimension by sensing monitoring motion of the subject during the period of non-supervision,
    and wherein:
    sensing the training motion comprises sensing training accelerometer data in at least one dimension; and
    sensing monitoring motion comprises sensing monitoring accelerometer data in the at least one dimension,
    and wherein the at least one dimension comprises at least two dimensions, and further including:
        determining training mean and variance of the training motion data in the at least two dimensions;
        transforming the training motion data into training amplitude data;
        creating training histogram data from the training amplitude data;
        fitting a training curve to the training amplitude data;
        determining training shape and scale based on the training curve;
        determining monitoring mean and variance of the monitoring motion data in the at least two dimensions;
        transforming the monitoring motion data into monitoring amplitude data;
        creating monitoring histogram data from the monitoring amplitude data;
        fitting a monitoring curve to the monitoring amplitude data;
        determining monitoring shape and scale based on the monitoring curve; and
        including comparing the monitoring shape and scale parameters to the shape and scale classification rules to determine if drug cravings are present.

2. The wearable device of claim 1, wherein:
    the microprocessor transmits classification data from the wearable device to a remote site during the unsupervised period;
    at the remote site, the classification data is processed using a deep neural network to refine the training set classification rules; and
    the remote site provides alerts to the subject cell phone based on the processed classification data.

3. The wearable device of claim 1, wherein:
    during the unsupervised period the microprocessor applies deep neural network processing to refine the classification rules; and
    the microprocessor provides alerts to the subject cell phone based on the refined classification rules.

4. The wearable device of claim 1, wherein:
generating training statistics comprises computing training mean and training variance of the training accelerometer data and determining the classification rules of the training statistics comprises determining classification rules of the mean and the variance of the training mean and the training variance; and
generating monitoring statistics comprises computing monitoring mean and monitoring variance of the monitoring accelerometer data and comparing the monitoring statistics comprises comparing the monitoring mean and the monitoring variance to the classification rules.

5. The wearable device of claim 4, further including:
collecting training Electrodermal Response (EDR) and training temperature data during the period of no drug use;
determining a training EDR mean and variance and a training temperature mean and variance;
including the training EDR mean and variance and the training temperature mean and variance in determining the classification rules;
collecting monitoring EDR and monitoring temperature data during the period of non-supervision;
determining monitoring EDR and monitoring temperature mean and variance from the monitoring EDR and the monitoring temperature data; and
including comparing the monitoring EDR mean and variance and monitoring temperature mean and variance to the classification rules to determine if drug cravings are present.

6. The wearable device of claim 5, wherein the training data and the monitoring data is collected and processed in windows having a length between three and seven minutes.

7. The wearable device of claim 6, wherein the training data and the monitoring data is collected and processed in windows having a length of about five minutes.

8. The wearable device of claim 1, wherein;
transforming the training motion data into training amplitude data comprises transforming the training motion data into training amplitude data using a Hilbert transform; and
transforming the monitoring motion data into monitoring amplitude data comprises transforming the monitoring motion data into monitoring amplitude data using a Hilbert transform.

9. The wearable device of claim 1, wherein;
transforming the training motion data into training amplitude data comprises transforming the training motion data into training amplitude data using a wavelet transform; and
transforming the monitoring motion data into monitoring amplitude data comprises transforming the monitoring motion data into monitoring amplitude data using a wavelet transform.

10. The wearable device of claim 1, wherein:
fitting a training curve to the training amplitude data comprises fitting a gamma function to the training amplitude data; and
fitting a monitoring curve to the monitoring amplitude data comprises fitting a gamma function to the training amplitude data.

11. A wearable device for detecting craving of a subject, comprising:
a housing including:
at least one sensor selected from the group consisting of an accelerometer, a thermopile sensor, and a pulse oximeter sensor
at least one subject button selected from the group consisting of a subject stress input button and a subject craving input button; and
a microprocessor electrically connected to the at least one sensor and the at least one subject button;
wireless communications between the microprocessor and at least one of a subject cell phone, a clinician, and a cloud,
wherein:
during a supervised period, the patient presses the input button while experiencing stress or cravings, and the microprocessor processes signals from the at least one sensor while the input button is pressed to determine training set classification rules; and
during an unsupervised period:
the microprocessor processes signals from the at least one sensor to determine characteristics of the unsupervised sensor data; and
the microprocessor compares the characteristics of the unsupervised sensor data to the training set classification rules; and
at least one element selected from the group consisting of the microprocessor, the clinician, and the cloud, provides alerts to the subject cell phone based on the comparison,
and wherein:
processing the signals from the at least one sensor and the at least one input buttons to determine training set classification rules during the supervised period comprises:
producing training motion data in at least one dimension by sensing the training motion of the subject during a period of no drug use;
generating training statistics of the training motion data during the period of no drug use; and
determining classification rules for the training statistics during the period of no drug use; and
processing signals from the at least one sensor to determine characteristics of the unsupervised sensor data comprises producing monitoring motion data in the at least one dimension by sensing monitoring motion of the subject during the period of non-supervision,
and wherein:
sensing the training motion comprises sensing training accelerometer data in at least one dimension; and
sensing monitoring motion comprises sensing monitoring accelerometer data in the at least one dimension,
and wherein:
generating training statistics comprises computing training mean and training variance of the training accelerometer data and determining the classification rules of the training statistics comprises determining classification rules of the mean and the variance of the training mean and the training variance; and
generating monitoring statistics comprises computing monitoring mean and monitoring variance of the monitoring accelerometer data and comparing the monitoring statistics comprises comparing the monitoring mean and the monitoring variance to the classification rules,
and wherein the at least one dimension comprises at least two dimensions, and further including:
determining training phase correlation between the at least two dimensions;

determining training classification rules further based on the training phase correlation;
determining monitoring phase correlation between the at least two dimensions;
including comparing the monitoring phase correlation to the classification rules to determine if the drug cravings are present.

12. A wearable device for detecting stress or craving of a subject, comprising:
a housing including:
at least one sensor selected from the group consisting of an accelerometer, a thermopile sensor, and a pulse oximeter sensor
at least one subject button selected from the group consisting of a subject stress input button and a subject craving input button; and
a microprocessor electrically connected to the at least one sensor and the at least one subject button;
the wearable device configured for wireless communications between the microprocessor and a subject cell phone, wherein:
during a supervised period of no drug use:
a subject wearing the wearable device and the pressing the input button while experiencing stress or cravings;
the wearable device producing accelerometer data by sensing motion of the subject;
transforming the accelerometer data into training amplitude data;
creating training histogram data from the training amplitude data;
fitting a training curve to the training histogram data;
determining shape and scale classification rules based on the training curve; and
during an unsupervised period:
the microprocessor processes signals from the accelerometer to determine monitoring motion data;
transforming the monitoring motion data into monitoring amplitude data;
creating monitoring histogram data from the monitoring amplitude data;
fitting a monitoring curve to the monitoring amplitude data;
determining monitoring shape and scale based on the monitoring curve;
comparing monitoring shape and scale to the shape and scale classification rules to determine if stress or cravings are present; and
providing alerts to the subject cell phone when stress or cravings are present based on the comparison.

13. The wearable device of claim 12, wherein the accelerometer data is 2 dimensional accelerometer data.

14. The wearable device of claim 12, wherein the accelerometer data is 3 dimensional accelerometer data.

* * * * *